United States Patent
Hantash

(10) Patent No.: US 10,155,982 B2
(45) Date of Patent: Dec. 18, 2018

(54) METHOD FOR DETECTING CYSTIC FIBROSIS

(75) Inventor: Feras Hantash, Dana Point, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

(21) Appl. No.: 13/312,821

(22) Filed: Dec. 6, 2011

(65) Prior Publication Data

US 2012/0094846 A1 Apr. 19, 2012

Related U.S. Application Data

(63) Continuation of application No. 10/942,757, filed on Sep. 16, 2004, now Pat. No. 8,092,996.

(51) Int. Cl.
| | |
|---|---|
| *C12Q 1/68* | (2018.01) |
| *C07H 21/04* | (2006.01) |
| *C12P 19/34* | (2006.01) |
| *C12Q 1/6883* | (2018.01) |
| *C12Q 1/6858* | (2018.01) |

(52) U.S. Cl.
CPC ......... *C12Q 1/6883* (2013.01); *C12Q 1/6858* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,541,308 | A | 7/1996 | Hogan et al. |
| 5,707,806 | A * | 1/1998 | Shuber .................. 435/6.11 |
| 5,945,526 | A | 8/1999 | Lee et al. |
| 2003/0235834 | A1 | 12/2003 | Dunlop et al. |
| 2004/0110138 | A1 | 6/2004 | Lem et al. |
| 2004/0126760 | A1 | 7/2004 | Broude |
| 2006/0057593 | A1 * | 3/2006 | Hantash .................... 435/6 |

FOREIGN PATENT DOCUMENTS

WO WO 2004/040013 A1 5/2004

OTHER PUBLICATIONS

Casals et al (Human Genet (1995) vol. 95, pp. 205-211).*
Gordy et al (Genetics in Medicine (2001) vol. 3, pp. 149-154).*
CFTR genecard (http://www.genecards.org/cgi-bin/carddisp.pl?gene=CFTR&keywords=cftr, downloaded Jul. 5, 2016).*
Diffenbach (PCR methods and Applications (1993) vol. 3, pp. S30-S37).*
Roux et al(PCR Methods and Applications (1995) vol. 4, pp. s185-s194).*
Audrézet et al., "Genomic Rearrangements in the CFTR Gene: Extensive Allelic Heterogeneity and Diverse Mutational Mechanisms" *Hum Mutat.* 23(4):343-357 (2004).
Benner et al., Evolution, language and analogy in functional genomics. Trends in Genetics, 17(7):414-418, (2001).
Boat et al, "Cystic Fibrosis." Chapter 108, The Metabolic Basis of Inherited Disease, 6th ed, pp. 2649-2680, McGraw Hill, NY (1989).
Buck et al., Design Strategies and Performance of Custom DNA Sequencing Primers, BioTechniques, 27(3):528-536 (1999).
Casals et al., Extensive analysis of 40 infertile patients with congenital absence of the vas deferens: in 50% of cases only one CFTR allele could be detected, Hum Genet, 95:205-211 (1995).
CFTR Database, www.genet.sickkids.on.ca/cftr/PicturePage.html?domain_id=1; downloaded Nov. 12, 2009.
Charbonnier et al., MSH2 in Contrast to MLH1 and MSH6 Is Frequently Inactivated by Exonic and Promoter Rearrangements in Heriditary Nonpolyposis Colorectal Cancer, Cancer Research, 62:848-853 (2002).
Chevalier-Porst et al., 40 Kilobase Deletion (CF 40 kb del 4-10) Removes Exons 4 to 10 of the Cystic Fibrosis Transmembrane Conductance Regulator Gene, Human Mutation, 1:S291-S924 (1998).
Costes et al.,Prenatal Detection by Real-Time Quantitative PCR and Characterization of a New CFTR Deletion, 3600+15kbdel5.3kb (or CFTRdele19), Clinical Chemistry, 46(9):1417-1420 (2000).
Cotton et al., Reactivity of cytosine and thymine in single-base-pair mismatches with hydroxylamine and osmium tetroxide and its application to the study of mutations, Proc. Natl. Acad. Sci. USA, 85:4397-4401, (1988).
Dieffenbach, General concepts for PCR primer design. PCR Methods and Applications, vol. 3, p. s185-s194, (1993).
Hafner et al., "Isothermal Amplification and Multimerization of DNA by Bst DNA Polymerase" *Biotechniques* 30(4):852-867 (2001).
He et al., Primers are decisive for sensitivity of PCR, Biotechniques, 17(1): 82-85, (1994).
Ju et. al. "Fluorescence energy transfer dye-labeled primers for DNA sequencing and analysis", *Proc. Nat'l Acad. Sci. USA* 92:4347-4351 (1995).
Liu et al., "Characterization of the segmental duplication LCR7-20 in the human genome" *Genomics* 83:262-269 (2004).
Oxford Medical Dictionary, p. 616, (1997).
Roux et al, PCR Methods and Applications, vol. 4, p. s185-s194, (1995).
Saiki, R., "Amplification of Genomic DNA" *PCR Protocols: A Guide to Methods and Applications* pp. 13-20 (1990).
Shackelton et al., Identification of Rare and Novel Mutations in the CFTR Genes of CF Patients in Southern England, Human Mutation, 3:141-151 (1994).
Stears et al., "A novel, sensitive detection system for high-density microarrays using dendrimer technology" *Physiol Genomics,* 3:93-99 (2000).

(Continued)

*Primary Examiner* — Steven Pohnert
(74) *Attorney, Agent, or Firm* — Foley & Lardner LLP

(57) ABSTRACT

The present invention relates to methods for amplifying various regions of the cystic fibrosis transmembrane regulator (CFTR) gene. Methods are provided for amplifying one or all 27 exons of the CFTR gene and a portion of the CFTR promoter region in a single tube. The method can identify the presence or absence of CF deletions or insertions in a sample and assist in the diagnosis of a genetic predisposition to cystic fibrosis.

11 Claims, No Drawings
Specification includes a Sequence Listing.

(56) References Cited

OTHER PUBLICATIONS

Struewing et al., Founder BRCA1/2 Mutations among Male Patients with Breast Cancer in Israel, Am. J. Hum. Genet., 65:1800-1802 (1999).
Thomas et al., Comparative analyses of multi-species sequences from targeted genomic regions. Nature, 424:788-793 (2003).
Vandesompele et al., Accurate normalization of real-time quantitative RT-PCR data by geometric averaging of multiple internal control genes, Genome Biology, 3(7):research0034.1-0034.11 (2002).
Wharam et al., "Specific detection of DNA and RNA targets using a novel isothermal nucleic acid amplification assay based on the formation of a three-way junction structure" *Nucleic Acids Res.* 29(11):2-8 (2001).
Zielenski, et al., "Genomic DNA Sequence of the Cystic Fibrosis Transmembrane Conductance Regulator (CFTR) Gene" *Genomics* 10:214-228 (1991).
Zielenski et al., Cystic Fibrosis: Genotypic and Phenotypic Variations, Annu. Rev. Genetics, 29:777-807 (1995).
U.S. Notice of Allowance dated Sep. 21, 2011 for U.S. Appl. No. 10/942,757.
U.S. Final Office Action dated Oct. 12, 2010 for U.S. Appl. No. 10/942,757.
U.S. Non-Final Office Action dated Nov. 19, 2009 for U.S. Appl. No. 10/942,757.
U.S. Non-Final Office Action dated Mar. 4, 2009 for U.S. Appl. No. 10/942,757.
U.S. Final Office Action dated Feb. 22, 2008 for U.S. Appl. No. 10/942,757.
U.S. Non-Final Office Action dated Jun. 4, 2007 for U.S. Appl. No. 10/942,757.
U.S. Non-Final Office Action dated Nov. 17, 2006 for U.S. Appl. No. 10/942,757.
Dork et al., Characterization of a novel 21-kb deletion, CFTRdele2,3[21 kb], in the CFTR gene; a cystic fibrosis mutation of Slavic origin common in Central and East Europe. Human Genetics, 106:259-268, 2000.
Bozon, D., Mutation details for 3199del6, Cystic Fibrosis Mutation Database, submitted 1998.
Casals et al., Mutation details for E3278del, Cystic Fibrosis Mutation Database, submitted 1998.
Claustres et al., Mutation details for 4382delA, Cystic Fibrosis Mutation Database, submitted 1992.
Claustres et al., Mutation details for 3195del6, Cystic Fibrosis Mutation Database, submitted 1994.
Claustres et al., Mutation details for 4332delTG, Cystic Fibrosis Mutation Database, submitted 1998.
Cuppens et al., Mutation details for 2721del11, Cystic Fibrosis Mutation Database, submitted 1992.
Dayangac et al., Mutation details for 1767del6, Cystic Fibrosis Mutation Database, submitted 2002.
Dean et al., Mutation details for 852del22, Cystic Fibrosis Mutation Database, submitted 1990.
Desgorges et al., Mutation details for 3196del54, Cystic Fibrosis Mutation Database, submitted 1995.
Doerk et al., Mutation details for 3130del15, Cystic Fibrosis Mutation Database, submitted 2002.
Dork et al., Mutation details for 2991del32, Cystic Fibrosis Mutation Database, submitted 1992.
Dork et al., Mutation details for [delta]L453, Cystic Fibrosis Mutation Database, submitted 1995.
Faucz et al., Mutation details for 232del18, Cystic Fibrosis Mutation Database, submitted 1996.
Feldman et al., Mutation details for [delta]D192, Cystic Fibrosis Mutation Database, submitted 1995.
Ferec et al, Mutation details for 4172delGC, Cystic Fibrosis Mutation Database, submitted 1993.
Ferec et al., Mutation details for 2766del8, Cystic Fibrosis Mutation Database, submitted 1994.
Ghanem et al., Mutation details for 3293delA, Cystic Fibrosis Mutation Database, submitted 1992.
Girodon et al., Mutation details for 816delCTC, Cystic Fibrosis Mutation Database, submitted 1999.
Hantash et al., Mutation details for Del exon 22-24, Cystic Fibrosis Mutation Database, downloaded Nov. 12, 2009.
Hermans et al., Mutation details for [delta]L1260, Cystic Fibrosis Mutation Database, submitted 1993.
Ozgul et al., Mutation details for 124del23bp, Cystic Fibrosis Mutation Database, 1993.
Scheffer et al., Mutation details for 1294del7, Cystic Fibrosis Mutation Database, submitted 1996.
Schwarz et al., Mutation details for 3922del10—>C, Cystic Fibrosis Mutation Database, submitted 1996.
Seia et al., Mutation details for 1845delAG/1848delGA, Cystic Fibrosis Mutation Database, submitted 1999.
Shoshani et al., Mutation details for 4010del4, Cystic Fibrosis Mutation Database, submitted 1994.
Varon et al., Mutation Details for 591del18, Cystic Fibrosis Mutation Database, submitted 1994.
Witt et al., Mutation Details for 3131del15, Cystic Fibrosis Mutation Database, submitted 1994.
Yoshimura et al., Mutation Details for 1540del10, Cystic Fibrosis Mutation Database, submitted 1999.
Zielenski et al., Mutation Deteiles for TAGGTAdel2622+2, Cystic Fibrosis Mutation Database, submitted 1998.

* cited by examiner

METHOD FOR DETECTING CYSTIC FIBROSIS

CROSS REFERENCE TO RELATED PATENT APPLICATIONS

This application is a continuation of U.S. Ser. No. 10/942,757, filed Sep. 16, 2004, incorporated herein by reference in its entirety.

FIELD OF THE INVENTION

The present invention relates to methods and nucleotide sequences for amplifying various regions of the cystic fibrosis transmembrane regulator (CFTR) gene to identify the presence or absence of CFTR gene deletions or duplications in a biological sample.

BACKGROUND OF THE INVENTION

The following description of the background of the invention is provided simply as an aid in understanding the invention and is not admitted to describe or constitute prior art to the invention.

Cystic fibrosis (CF) is the most common severe autosomal recessive genetic disorder in the Caucasian population. It affects approximately 1 in 2,500 live births in North America (Boat et al, The Metabolic Basis of Inherited Disease, 6th ed, pp 2649-2680, McGraw Hill, N.Y. (1989)). Approximately 1 in 25 persons are carriers of the disease. The major symptoms of cystic fibrosis include chronic pulmonary disease, pancreatic exocrine insufficiency, and elevated sweat electrolyte levels. The symptoms are consistent with cystic fibrosis being an exocrine disorder. Although recent advances have been made in the analysis of ion transport across the apical membrane of the epithelium of CF patient cells, it is not clear that the abnormal regulation of chloride channels represents the primary defect in the disease.

The gene for CF has been localized to a 250,000 base pair genomic sequence present on the long arm of chromosome 7. This sequence encodes a membrane-associated protein called the "cystic fibrosis transmembrane regulator" (or "CFTR"). There are greater than 1000 different mutations in the CFTR gene, having varying frequencies of occurrence in the population, presently reported to the Cystic Fibrosis Genetic Analysis Consortium. These mutations exist in both the coding regions (e.g., ΔF508, a mutation found on about 70% of CF alleles, represents a deletion of a phenylalanine at residue 508) and the non-coding regions (e.g., the 5T, 7T, and 9T mutations correspond to a sequence of 5, 7, or 9 thymidine bases located at the splice branch/acceptor site of intron 8) of the CFTR gene. Comparison of the CFTR genomic and cDNA sequences confirms the presence of 27 exons. The exons are numbered 1, 2, 3, 4, 5, 6a, 6b, 7, 8, 9, 10, 11, 12, 13, 14a, 14b, 15, 16, 17a, 17b, 18, 19, 20, 21, 22, 23, and 24. Each intron is flanked by the consensus GT-AG splice-site sequence as previously reported (Zielenski, et al., (1991) Genomics 10, 214-228).

Methods for detecting CFTR gene mutations have been described. See e.g., Audrezet et al., "Genomic rearrangements in the CFTR gene: extensive allelic heterogeneity and diverse mutational mechanisms" Hum Mutat. 2004 April; 23(4):343-57; PCT WO 1004/040013 A1 and corresponding US application #20040110138; titled "Method for the detection of multiple genetic targets" by Spiegelman and Lem; US patent application No. 20030235834; titled "Approaches to identify cystic fibrosis" by Dunlop et al.; and US patent application No. 20040126760 titled "Novel compositions and methods for carrying out multiple PCR reactions on a single sample" by N. Broude. Improved methods are needed to efficiently detect the variety of CFTR gene defects which underlie CF.

SUMMARY OF THE INVENTION

Provided are methods of detecting deletions or duplications in the CFTR gene. The method includes (a) amplifying multiple target segments of the CFTR gene in a single vessel using oligonucleotide primer pairs specific to each of the target segments in a multiplex polymerase chain reaction (PCR). In a preferred embodiment, amplification for all primers to be evaluated is conducted in a single tube. In a preferred embodiment, the target segments represent individual exons or portions of exons of the CFTR gene. The target segment also may include the CFTR promoter region. The multiplex amplification may also include a primer pair for at least one internal control target segment of nucleic acid that does not correspond to the CFTR gene. In accordance with particular embodiments, amplification may be performed without the aid of complex PCR methods such as nested PCR and touchdown PCR.

The present CFTR assay can detect one or more or all of the 27 exons of the CFTR gene. In some embodiments, the method can be used to detect at least 7 target segments in a single multiplex PCR, the segments representing at least 5 different exons of the CFTR gene. In other embodiments, the method can be used to detect at least 17 target segments of the CFTR gene in a single multiplex PCR. In yet other embodiments, the method can be used to detect at least 17 target segments in a single multiplex PCR representing at least 15 different exons of the CFTR gene. In still yet other embodiments, the method can be used to detect at least 28 target segments of the CFTR gene in a single multiplex PCR. In some embodiments, the 28 target segments may together represent at least 20 different exons of the CFTR gene. In yet other embodiments, all 27 exons of the CFTR gene are amplified in a single multiplex PCR.

Another target segment for amplification is the CFTR promoter region. The term "CFTR promoter region" as used herein refers to a segment of the CFTR gene representing at least the first 250 nucleotides upstream from the translation start site. In other embodiments, the promoter region may include the first 250 nt, first 300 nt, first 350 nt, first 400 nt, first 450 nt, first 500 nt, first 1 kb, first 5 kb, first 10, kb, first 15, kb, first 20, kb, first 21 kb or first 22 kb of sequence directly upstream of the start codon. A deletion of the promoter region as defined herein may be accompanied by deletion of downstream exons/introns but not all of the CFTR gene. In some embodiments, the coordinate deletion involving the CFTR promoter region and downstream CFTR gene sequence involves about less than 10 exons, and more typically involves less than 5 exons. Deletions or duplications of the CFTR promoter region may be detected using primers that flank the deleted or duplicated sequence. In a preferred embodiment, a promoter deletion or duplication involves a segment of at least four or more nucleotides, more preferably 5 or more, more preferably 8 or more, and even more preferably 12 or more nucleotides.

The method also can include detection of one or more non-CFTR gene segments to provide an "internal control" for the multiplex amplification. In a preferred embodiment, the internal controls can be segments of various genes. Such segments can include an exon from the Tay Sachs HEXA gene, an exon from coagulation factor II gene and/or an exon from the coagulation factor V gene. Other internal controls can be used. Preferably, the internal controls reside on different chromosomes from the CFTR gene, or on the short arm of chromosome 7.

Following amplification, the various target segments are separately identified and evaluated for the relative amount of the segment present versus that for a control (i.e., wildtype) CFTR gene. In a preferred embodiment, the amplified segments are separated by size such as by gel electrophoresis and or by color.

A substantial increase in the amount of a CFTR target segment identified means that the segment has been duplicated while a substantial decrease in the amount of a CFTR target segment identified means that the target segment has been deleted. The term "substantial decrease" or "substantial increase" means a decrease or increase of at least about 30-50%. Thus, deletion of a single CFTR exon would appear in the assay as a signal representing for example of about 50% of the same exon signal from an identically processed sample from an individual with a wildtype CFTR gene. Conversely, amplification of a single exon would appear in the assay as a signal representing for example about 150% of the same exon signal from an identically processed sample from an individual with a wildtype CFTR gene.

In a preferred embodiment, at least one primer of each primer pair in the PCR is labeled with a detectable moiety. Thus, following amplification, the various target segments can be identified by size and color. The detectable moiety is preferably a fluorescent dye. In some embodiments, different pairs of primers in a multiplex PCR may be labeled with different distinguishable detectable moieties. Thus, for example, HEX and FAM fluorescent dyes may be present on different primers in the multiplex PCR and associated with the resulting amplicons. In other embodiments, the forward primer will be labeled with one detectable moiety, while the reverse primer will be labeled with a different detectable moiety, e.g. FAM dye for Forward primer and Hex due for Reverse primer. Use of different detectable moieties is useful for discriminating between amplified products which are of the same length or are very similar in length. Thus, in a preferred embodiment, at least two different fluorescent dyes are used to label different primers used in a single amplification. In still another embodiment, the normal (wt) control primers can be labeled with one moiety, while the patient (or test sample) primers can be labeled with a different moiety, to allow for mixing of both samples (post PCR) and the simultaneous detection and comparison of signals of normal and test sample. In a modification of this embodiment, the primers used for wt samples and patient samples can be switched to allow for further confirmation of results.

Analysis of amplified products from multiplex PCR reactions can be performed using an automated DNA analyzer such as an automated DNA sequencer (e.g., ABI PRISM 3100 Genetic Analyzer) which can evaluate the amplified products based on size (determined by electrophoretic mobility) and/or respective fluorescent label.

The above methods of detecting deletions or duplications of various exons of the CFTR gene may used for diagnosing a genetic basis for cystic fibrosis. In one approach, the method for diagnosing a genetic basis to cystic fibrosis (CF) is performed by analyzing a sample comprising nucleic acids from an individual to determine if the promoter region of the CFTR gene contains deleted or duplicated sequence and correlating the deleted or duplicated sequence with CF predisposition.

Also provided are novel deletions involving the CFTR promoter region and associated downstream exon(s) that can be used in diagnosing a genetic basis for CF. These promoter/exon mutations include a deletion in a segment of the CFTR promoter region including the adjoining CFTR exon 1 or a deletion in a segment of the CFTR promoter region including the adjoining CFTR exons 1 and 2. The deletion involving the promoter region and exon 1 comprises at least 1,800 nucleotides in length of which at least 1,630 nucleotides represents sequence from the CFTR promoter region. The deletion involving the promoter and exons 1 and 2 comprises at least 28,000 nucleotides in length of which at least 3,570 nucleotides represents sequence from the CFTR promoter region.

These deletions may be detected using the methods disclosed herein or other methods of deletion detection well known in the art.

Further provided for use in diagnosing a genetic basis for CF is are novel deletions involving CFTR exons 22, 23, and 24 but no other CFTR exons. Sequence 3' to exon 24 also may be deleted. These deletions may be detected using the methods disclosed herein or other methods of deletion detection well known in the art.

Oligonucleotides or combinations of oligonucleotides that are useful as primers in the method are also provided. These oligonucleotides are provided as substantially purified material.

Kits comprising oligonucleotides for performing amplifications as described herein also are provided.

The term "deletion" as used herein encompasses a mutation that removes one or more nucleotides from nucleic acid. Conversely, the term "duplication" refers to a mutation that inserts one or more nucleotides of identical sequence directly next to this sequence in the nucleic acid. In a preferred embodiment, a deletion or duplication involves a segment of four or more nucleotides.

The term "primer" as used herein means a sequence of nucleic acid, preferably DNA, that hybridizes to a substantially complementary target sequence and is recognized by DNA polymerase to begin DNA replication. The term primer as used herein includes all forms of primers that may be synthesized including peptide nucleic acid primers, locked nucleic acid primers, phosphorothioate modified primers, labeled primers, and the like.

The term "amplify" as used herein with respect to nucleic acid sequences, refers to methods that increase the representation of a population of nucleic acid sequences in a sample. Nucleic acid amplification methods, such as PCR, isothermal methods, rolling circle methods, etc., are well known to the skilled artisan. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 Jun. 1; 29(11):E54-E54; Hafner et al., Biotechniques 2001 April; 30(4):852-6, 858, 860 passim; Zhong et al., Biotechniques 2001 April; 30(4): 852-6, 858, 860.

The terms "complementary" or "complementarity" as used herein with reference to polynucleotides (i.e., a sequence of nucleotides such as an oligonucleotide or a target nucleic acid) refers to the base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, for the sequence "5'-A-G-T-3'" is complementary to the sequence "3'-T-C-A-5'." Certain bases not commonly found in natural nucleic acids may be included in the nucleic acids described herein; these include, for example, inosine, 7-deazaguanine, Locked Nucleic Acids (LNA), and Peptide Nucleic Acids (PNA). Complementary need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be a sequence of RNA complementary to the DNA sequence or its complement sequence, and can also be a cDNA.

The term "substantially complementary" as used herein means that two sequences hybridize under stringent hybridization conditions. The skilled artisan will understand that substantially complementary sequences need not hybridize along their entire length. In particular, substantially complementary sequences comprise a contiguous sequence of bases that do not hybridize to a target sequence, positioned 3' or 5' to a contiguous sequence of bases that hybridize under stringent hybridization conditions to a target sequence.

The term "flanking" as used herein means that a primer hybridizes to a target nucleic acid adjoining a region of interest sought to be amplified on the target. The skilled artisan will understand that preferred primers are pairs of primers that hybridize 3' from a region of interest, one on each strand of a target double stranded DNA molecule, such that nucleotides may be added to the 3' end of the primer by a suitable DNA polymerase. Primers that flank a CF exon are generally designed not to anneal to the exon sequence but rather to anneal to sequence that adjoins the exon (e.g. intron sequence). However, in some cases, amplification primer may be designed to anneal to the exon sequence. The location of primer annealing for many primer pairs that may be used with the methods is shown in Table 1.

The phrase "comprise sequence from all or a portion of" in reference to an exon means that the sequence represents all of the exon or at least 10 bases of the exon. In other embodiments, most of the exon is amplified, generally greater than 50%, greater than 60%, greater than 70%, greater than 80%, greater than 90% and greater than 95%.

The term "specific" as used herein in reference to an oligonucleotide primer means that the primer hybridization sequence of the primer has at least 12 bases of sequence identity with a portion of the nucleic acid to be amplified when the oligonucleotide and the nucleic acid are aligned. An oligonucleotide primer that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity.

The term "multiplex PCR" as used herein refers to amplification of two or more products which are each primed using a distinct primers pair.

The term "hybridize" or "specifically hybridize" as used herein refers to a process where two complementary nucleic acid strands anneal to each other under appropriately stringent conditions. Hybridizations are typically and preferably conducted with probe-length nucleic acid molecules, preferably 20-100 nucleotides in length, more preferably 18-50 nucleotides in length. Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementary will stably hybridize, while those having lower complementary will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

The term "stringent hybridization conditions" as used herein refers to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5× Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

The term "sense strand" as used herein means the strand of double-stranded DNA (dsDNA) that includes at least a portion of a coding sequence of a functional protein. "Antisense strand" means the strand of dsDNA that is the reverse complement of the sense strand.

The term "forward primer" as used herein means a primer that anneals to the anti-sense strand of dsDNA. A "reverse primer" anneals to the sense-strand of dsDNA.

The term "isolated" as used herein with respect to a nucleic acid (e.g., an RNA, DNA or a mixed polymer) is one which is substantially separated from other cellular components which naturally accompany such nucleic acid. The term embraces a nucleic acid sequence which has been removed from its naturally occurring environment, and includes recombinant or cloned DNA isolates, oligonucleotides, and chemically synthesized analogs or analogs biologically synthesized by heterologous systems.

The term "substantially pure" as used herein means a nucleic acid, represents more than 50% of the nucleic acid in a sample. The nucleic acid sample may exist in solution or as a dry preparation.

The term "coding sequence" as used herein means a sequence of a nucleic acid or its complement, or a part thereof, that can be transcribed and/or translated to produce the mRNA for and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the encoding sequence can be deduced therefrom.

The term "non-coding sequence" as used herein means a sequence of a nucleic acid or its complement, or a part thereof, that is not transcribed into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, etc.

The term "carrier state" as used herein means a person who contains one CFTR allele that is a mutant CF nucleic acid sequence, but a second allele that is not a mutant CF nucleic acid sequence. CF is an "autosomal recessive" disease, meaning that a mutation produces little or no phenotypic effect when present in a heterozygous condition with a non-disease related allele, but produces a "disease state" when a person is homozygous or compound heterozygote, i.e., both CFTR alleles are mutant CF nucleic acid sequences.

The term "wildtype" as used herein with respect to the CFTR gene or a locus thereof refers to the CFTR gene sequence which is found in NCBI GenBank locus IDs M58478 (HUMCFTC), AC000111 and AC000061. The cDNA for the CFTR gene is found in Audrezet et al., Hum. Mutat. (2004) 23 (4), 343-357. Alleic variant is one that is "non-disease causing" and reaches a frequency of 1% or more in the population.

The term "familial history" as used herein means the individual has immediate family members including parents and siblings. Family history also may include grandparents.

The term "about" as used herein means in quantitative terms plus or minus 10%.

DETAILED DESCRIPTION OF THE INVENTION

Provided are methods for detecting deletions or duplications in the CFTR gene. The method includes amplifying multiple target segments of the CFTR gene in a single vessel (i.e. as a multiplex polymerase chain reaction) using oligonucleotide primer pairs specific to each of the target segments. In accordance with the method, the amplified target segments are identified and the amount of each target segment amplified versus that for a wildtype CFTR gene are determined. A substantial decrease or increase in the amount of detectable target segment observed versus that for a normal CFTR gene indicates a deletion or duplication, respectively, of the CFTR segment in the sample.

Accordingly, there is provided a method for detecting deletions or duplications in the cystic fibrosis transmembrane conductance regulator gene (CFTR) in a sample comprising nucleic acids, the method comprising: (a) amplifying target segments of the CFTR gene in a single tube using an oligonucleotide primer pair specific to each of the target segments; and (b) identifying the amplified target segments and determining the amount of each target segment amplified versus that for a normal CFTR gene, wherein a substantial decrease or increase in the amount of detectable target segment observed versus that for a normal CFTR gene indicates a deletion or duplication, respectively, of the CFTR segment in the sample.

The sample to be analyzed may consist of or comprise blood, sera, urine, feces, epidermal sample, vaginal sample, skin sample, cheek swab, sperm, amniotic fluid, cultured cells, bone marrow sample and/or chorionic villi, cultured cells, and the like. Fixed or frozen tissues also may be used. Whole blood samples of about 0.5 to 5 ml colleted with EDTA, ACD or heparin as anti-coagulant are suitable. Amniotic fluid of 10-15 ml, cultured cells which are 80-100% confluent in two T-25 flasks and 25 mg of chorionic villi are useful sample amounts for processing.

The sample may be processed to release or otherwise make available a nucleic acid for detection as described herein. Such processing may include steps of nucleic acid manipulation, e.g., preparing a cDNA by reverse transcription of RNA from the biological sample. Thus, the nucleic acid to be amplified by the methods of the invention may be genomic DNA, cDNA, single stranded DNA or mRNA.

In one embodiment, at least 7 target segments of the CFTR gene are evaluated. In one approach, the 7 target segments together represent at least 5 different exons of the CFTR gene. In another embodiment, at least 17 target segments of the CFTR gene are evaluated. In another approach, the 17 target segments together represent at least 15 different exons of the CFTR gene are evaluated. In yet another embodiment, at least 28 target segments of the CFTR gene. In yet another approach, the 28 target segments together represent at least 20 different exons of the CFTR gene and at least one region of the promoter of the CFTR gene.

In another embodiment, the multiplex amplification can include a primer pair specific for a CFTR intronic segment. In one approach the CFTR intronic segment is a segment near to the beginning of exon 9. Intronic segment analysis can be useful to confirm exon duplication or deletion in particular cases when the deletion or duplication extends into the intronic region. In the case of exon 9 there is repeat sequence upstream, specifically TG repeat (typically 10-12 TG units) and a T repeat (5, 7 or 9 Ts) regions. Variation in TG repeat number and the T repeat number in different individuals sometimes causing the appearance of several fragments representing exon 9 when primers are placed at the ends of the exon and can lead to lowering of the amplified signal for F9.

Accordingly, the forward primer for amplifying CFTR Exon 9 has been designed to anneal to the intronic region upstream of Exon 9, starting at about 104 bases upstream of the exon. This segment upstream of exon 9 has not been reported to be involved in exon 9 pseudogene (Liu et al., (2003) Genomics 83:262-269). However, due to the nature of the various exon-9 related fragments that can appear because of the upstream repeat sequences, a further segment of intron 8 preceding exon 9 is included in the amplicon to confirm any down stream deletion or duplication involving exon 9 that would also encompass the upstream intronic sequence. The amplification involving a forward primer and a reverse primer in the intronic region directly upstream of exon 9 is referred to herein as "UpEx9." Thus, the method can evaluate by a single multiplex PCR, a total of at least 29 target segments, the segments representing 27 exons of the CFTR gene, the CFTR promoter region and UpEx9.

The multiplex amplification may include primers for amplifying one or more non-CFTR gene segments as an internal control. Such internal controls may include exon 1 of the coagulation factor 2 gene of chromosome 11 ("F2"), exon 10 of coagulation factor V of chromosome 11 ("F5") and/or exon 7 of the Tay Sachs HEXA gene of chromosome 15 ("TS"). In a preferred embodiment, all three of these exons may be amplified. Thus, the method can evaluate by a single multiplex PCR, a total of at least 32 target segments, the segments representing 27 exons of the CFTR gene, the CFTR promoter region, UpEx9 and three internal control exons.

To assist in identifying amplified segments, at least one primer from some or all of the primer pairs in the multiplex can be labeled with a detectable moiety. It would be evident to the skilled artisan that the detectable moiety could be attached in any manner of variety that does not interfere with the oligonucleotide to function as an amplification primer.

The phrase "detectable moiety" is used herein to denote any molecule (or combinations of molecules) that may be attached or otherwise associated with a molecule so that the molecule can be detected indirectly by detecting the detectable moiety. A detectable moiety can be a radioisotope (e.g., iodine, indium, sulfur, hydrogen etc.) a dye or fluorophor (e.g., cyanine, fluorescein, rhodamine), protein (e.g., avidin, antibody), enzyme (peroxidase, phosphatase, etc.), or any other agent that can be detected directly or indirectly. An enzyme is an example of a detectable moiety detected by indirect means. In this case, the enzyme is attached to the target nucleic acid and the presence of the enzyme is detected by adding an appropriate substrate that when acted upon by the enzyme, causes the substrate to change in color or to release a cleavage product that provides a different color from the original substrate.

The term "fluorescent detectable moiety" or "fluorophore" as used herein refers to a molecule that absorbs light at a particular wavelength (excitation frequency) and subsequently emits light of a longer wavelength (emission frequency). A fluorescent detectable moiety can be stimulated by a laser with the emitted light captured by a detector. The detector can be a charge-coupled device (CCD) or a confocal microscope, which records its intensity.

A useful detectable moiety is a cyanine dye such as Cy-5 and Cy-3, FAM, HEX, and the like. A detectable moiety may include more than one chemical entity such as in fluorescent resonance energy transfer (FRET). Resonance transfer results an overall enhancement of the emission intensity. For instance, see Ju et. al. (1995) Proc. Nat'l Acad. Sci. (USA) 92: 4347. To achieve resonance energy transfer, the first fluorescent molecule (the "donor" fluor) absorbs light and transfers it through the resonance of excited electrons to the second fluorescent molecule (the "acceptor" fluor). In one approach, both the donor and acceptor dyes can be linked together and attached to the oligo primer. Methods to link donor and acceptor dyes to a nucleic acid have been described previously, for example, in U.S. Pat. No. 5,945,526 to Lee et al. Donor/acceptor pairs of dyes that can be used include, for example, fluorescein/tetramethylrohdamine, IAEDANS/fluoroescein, EDANS/DABCYL, fluorescein/fluorescein, BODIPY FL/BODIPY FL, and Fluorescein/QSY 7 dye. See, e.g., U.S. Pat. No. 5,945,526 to Lee et al. Many of these dyes also are commercially available, for instance, from Molecular Probes Inc. (Eugene, Oreg.). Other dyes include Suitable donor fluorophores include 6-carboxyfluorescein (FAM), tetrachloro-6-carboxyfluorescein (TET), 2'-chloro-7'-phenyl-1,4-dichloro-6-carboxyfluorescein (VIC), and the like.

In another embodiment, signal amplification may be achieved using labeled dendrimers as the detectable moiety (see, e.g., Physiol Genomics 3:93-99, 2000). Fluorescently labeled dendrimers are available from Genisphere (Montvale, N.J.). These may be chemically conjugated to the oligonucleotide primers by methods known in the art.

The sequence of substantially pure nucleic acid primers which are DNA (or an RNA equivalent) and which are useful for amplifying the promoter region, each of the 27 exons of the CFTR gene, an intronic sequence directly upstream of CFTR exon 9 and various exons of the internal control target segment are shown in Table 1. The letter F or R at the end of the primer name indicates whether the primer is a forward (F) or reverse (R) PCR primer. FAM and HEX refer to fluorescent compounds chemically linked to the 5' end of the oligonucleotide.

TABLE 1

CFTR Assay Primer Sequences

| SEQ ID NO | Primer Name | Sequence | Hybridizes to: |
|---|---|---|---|
| 1 | CFDELPF | 5'-6-FAM/ACT GTC GCC CAC CTG CGG -3' | promoter |
| 2 | CFDELPR | 5'-CCG CAC ACC ACC CCT TCC -3' | promoter |
| 3 | CFDEL1F | 5'-6-FAM/AAT TGG AAG CAA ATG ACA TCA CAG -3' | exon 1 |
| 4 | CFDEL1R | 5'-TTC CTT TAC CCC AAA CCC AA -3' | intron 1 |
| 5 | CFDEL2F | 5'-6-FAM/CCT CTC TTT ATT TTA GCT GGA CCA GAC -3' | intron 1/exon 2 |
| 6 | CFDEL2R | 5'-TCA ACT AAA CAA TGT ACA TGA ACA TAC CT -3' | exon 2/intron 2 |
| 7 | CFDEL3F2 | 5'-6-FAM/GAA TGG GAT AGA GAG CTG GCT -3' | exon 3 |
| 8 | CFDEL3R | 5'-TGT ACA AAT GAG ATC CTT ACC CCT A -3' | exon 3/intron 3 |
| 9 | CFDEL4F | 5'-6-FAM/GAA GTC ACC AAA GCA GTA CAG CC -3' | Exon 4 |
| 10 | CFDEL4R | 5'-GCC TGT GCA AGG AAG TAT TAC CT -3' | Exon 4/Intron 4 |
| 11 | CFDEL5F | 5'-6-FAM/TTT AGA CTT TAA AGC TGT CAA GCC G -3' | Intron 4/.Exon 5 |
| 12 | CFDEL5R | 5'-CCG CCT TTC CAG TTG TAT AAT TTA T -3' | Intron 5 |
| 13 | CFDEL6aF | 5'-6-FAM/GGA CTT GCA TTG GCA CAT TT -3' | Exon 6a |
| 14 | CFDEL6aR | 5'-TGC TAC CTG TAC TTC ATC ATC ATT C -3' | Exon 6a/Intron 6a |
| 15 | CFDEL6bF | 5'-6-FAM/TGT AAA ACG ACG GCC AGT AGA TCA GAG AGC TGG GAA GAT CA -3' | Exon 6b |
| 16 | CFDEL6bR | 5'-GGT GGA AGT CTA CCA TGA TAA ACA T -3' | Intron 6b |
| 17 | CFDEL7F | 5'-6-FAM/AAC AGA ACT GAA ACT GAC TCG GA -3' | Exon 7 |
| 18 | CFDEL7R | 5'-GCA GCA TTA TGG TAC ATT ACC TGT A -3' | Exon 7/Intron 7 |
| 19 | CFDELEX8F2 | 5'-6-FAM/TTT TTT TTT TTT TTT ATA AGA TGT AGC ACA ATG AGA GTA AAG T -3' | Intron 7 |

TABLE 1-continued

CFTR Assay Primer Sequences

| SEQ ID NO | Primer Name | Sequence | Hybridizes to: |
|---|---|---|---|
| 20 | CFDEL8R | 5'-TAA AAA TTC TGA CCT CCT CCC A -3' | exon 8/intron 8 |
| 21 | CFDELex9F2 | 5'-6-FAM/TGG ATC ATG GGC CAT GTG C -3' | Intron 8 |
| 22 | CFDEL9R | 5'-CAA AAG AAC TAC CTT GCC TGC T -3' | intron 9 |
| 23 | CFDEL10F | 5'-6-FAM/TCC AGA CTT CAC TTC TAA TGG TGA -3' | Intron 9/exon 10 |
| 24 | CFDEL10R | 5'-GTG AAG GGT TCA TAT GCA TAA TCA A -3' | intron 10 |
| 25 | CFDEL11F | 5'-6-FAM/AGG ACA TCT CCA AGT TTG CAG A -3' | intron 10/exon 11 |
| 26 | CFDEL11R | 5'-GCA AAT GCT TGC TAG ACC AAT AAT T -3' | intron 11 |
| 27 | CFDEL12F | 5'-6-FAM/TGA CCA GGA AAT AGA GAG GAA ATG -3' | intron 11 |
| 28 | CFDEL12R | 5'-CTA TGA TGG GAC AGT CTG TCT TTC T -3' | intron 12 |
| 29 | CFDEL13F | 5'-6-FAM/GTG ATC AGC ACT GGC CCC AC -3' | Exon 13 |
| 30 | CFDEL13R | 5'-CCC CCA AGC GAT GTA TAC CT -3' | Intron 13 |
| 31 | CFDEL14aF | 5'-6-FAM/TTT TGA GTG CTT TTT TGA TGA TAT GGA GA -3' | Exon 14a |
| 32 | CFDEL14aR | 5'-AAC ATT CTT ACC TCT GCC AGA AAA -3' | Exon 14a/intron 14a |
| 33 | CFDEL14bF | 5'-6-FAM/GGA GGA ATA GGT GAA GAT GTT AGA A -3' | Intron 14a |
| 34 | CFDEL14bR | 5'-GGA GAA ATG AAA CAA AGT GGA TTA C -3' | Intron 14b |
| 35 | CFDEL15F | 5'-6-FAM/TTT TTT TTC ACT CCT CTT CAA GAC AAA GGG -3' | Exon 15 |
| 36 | CFDEL15R | 5'-TAC CTG CTT TCA ACG TGT TGA G -3' | Exon 15/Intron 15 |
| 37 | CFDEL16F | 5'-6-FAM/GCG TCT ACT GTG ATC AAA CTA GT -3' | Intron 15 |
| 38 | CFDEL16R | 5'-GGA CTT CAA CCC TCA ATC AAA TAA A -3' | Intron 16 |
| 39 | CFDEL17aF | 5'-6-FAM/TTC TCA CCA ACA TGT TTT CTT TGA TC -3' | Intron 16 |
| 40 | CFDEL17aR | 5'-GTC ATA CCT TCA GAT TCC AGT TGT T -3' | Exon 17a/Intron 17a |
| 41 | CFDEL17bF2 | 5'-6-FAM/TGG AAA TAT TTC ACA GGC AGG AGT C -3' | intron 17a/exon 17b |
| 42 | CFDEL17BR2 | 5'-CAT TTT ATT CAT TGA AAA TTT TTT ACT AAA ATG -3' | intron 17b |
| 43 | CFDEL18F2 | 5'-6-FAM/TAC TTA CTA TAT GCA GAG CAT TAT TCT ATT AGT AG -3' | Intron 17b |
| 44 | CFDEL18R | 5'-CTT ACC AAG CTA TCC ACA TCT ATG C -3' | Exon 18/Intron 18 |
| 45 | CFDEL19F | 5'-6-FAM/ATG CGA TCT GTG AGC CGA GT -3' | Exon 19 |
| 46 | CFDEL19R | 5'-CCC TCT GGC CAG GAC TTA TT -3' | Exon 19/Intron 19 |
| 47 | CFDEL20F | 5'-6-FAM/GTG GGC CTC TTG GGA AGA AC -3' | Exon 20 |
| 48 | CFDEL20R | 5'-GCT CAC CTG TGG TAT CAC TCC AA -3' | Exon 20/Intron 20 |
| 49 | CFDEL21F | 5'-6-FAM/TGT AAA ACG ACG GCC AGT CTT TTC TTT TTT GCT ATA GAA AGT ATT TAT TTT -3' | intron 20/exon 21 |
| 50 | CFDEL21R | 5'-CAG CCT TAC CTC ATC TGC AAC TT -3' | exon 21/intron 21 |
| 51 | CFDEL22F | 5'-6-FAM/GTT GGG CTC AGA TCT GTG ATA GA -3' | exon 22 |
| 52 | CFDEL22R | 5'-CAC ACT GGA TCC AAA TGA GCA C -3' | exon 22/intron 22 |
| 53 | CFDEL23F | 5'-6-FAM/CAT TAC TGT TCT GTG ATA TTA TGT GTG GTA -3' | intron 22 |
| 54 | CFDEL23R | 5'-CAA GGG CAA TGA GAT CTT AAG TAA -3' | intron 23 |
| 55 | CFDEL24F | 5'-6-FAM/AGA AGA GAA CAA AGT GCG GCA -3' | Exon 24 |

TABLE 1-continued

CFTR Assay Primer Sequences

| SEQ ID NO | Primer Name | Sequence | Hybridizes to: |
|---|---|---|---|
| 56 | CFDEL24R | 5'-TGT ATC TTG CAC CTC TTC TTC TGT C -3' | Exon 24 |
| 57 | Upex9F | 5'-/5HEX/TTT TTT TTT TTG TAA AAC GAC GGC CAG TTT CAG TCT TTA CTG AAA TTA AAA AAT CTT -3' | Intron 8 |
| 58 | Upex9R | 5'-ATA GCA TAC GGT TTC TAG AGG ACA TG -3' | Intron 8 |
| 59 | F5F | 5'-HEX/TTG AAG GAA ATG CCC CAT TAT TTA GCC AGG -3' | Intron 11 |
| 60 | F5R | 5'-TGC TTA ACA AGA CCA TAC TAC AGT GAC GT -3' | Exon 10 |
| 61 | F2F | 5'-6-FAM/AGG AGG ACC TGT CCT CCC AGA TGG T -3' | Sequence Upstream of exon 1 |
| 62 | F2R | 5'-CTG TCC AGC CAG GAG ACC CCA - 3' | Intron 1 |
| 63 | TSF | 5'-HEX/CAT TCT TAC CTG GTC CCC AGG ACA AAG -3' | Exon 7/Intron 8 |
| 64 | TSR | 5'-GTC CTA CAA CCC TGT CAC CCA CAT C -3' | Exon 7 |

Various subsets of the primer pairs from Table 1 may be used in a multiplex PCR. For example, primer sequences that can be used to verify a suspected CFTR promoter deletion or duplication and to asses the extent of such deletion or duplication. Primer pairs which evaluate three promoter regions upstream of region amplified by SEQ ID NO:1 and 2 primers, designated as UPr1, UPr2 and UPr3, are shown in Table 2. These may be combined in a mutiplex amplification with primer pairs for CFTR exons 1, 2, 3 and 4 and/or others. In addition, one may include any number of internal control primer pairs such as the three in Table 1.

TABLE 2

CFTR promoter and internal control primer concentrations in Master Mix

| SEQ ID NO: | Primer Name | Primer Sequence |
|---|---|---|
| 65 | UpPr1F | FAM-5'-GAA TTC AAA GGA AAA CAT AAG ATG CAA TTC -3' |
| 66 | UpPr1R | 5'-AAC ACA CAT TAC AGT CTT ACA AAG ATG TTT -3' |
| 67 | UpPr2F1 | FAM-5'-CCA CAC TAA CAG TTA TAA ACC AAA CAA CA -3' |
| 68 | UpPr2R | 5'-CAC CAG GAA AGA ATT TCA GCA TTT -3' |
| 69 | UpPr3F | FAM-5'-CTA AAA CAC TCC AAA GCC TTC TT -3' |
| 70 | UpPr3R | 5'-TTC AGG TTT AGG TGA GTG AAC TCC AA -3' |

The above methods of detecting deletions or duplications of various exons of the CFTR gene may used to detect a deletion or duplication involving a segment of the CFTR promoter region by itself or including CFTR exon 1 or CFTR exon 1 and 2. Accordingly, there is provided a method for detecting deletions or duplications in the promoter region of the cystic fibrosis transmembrane conductance regulator gene (CFTR) in a sample comprising nucleic acids, the method comprising: (a) amplifying a segment within a region of 250 nucleotides or more directly upstream of the CFTR start codon using an oligonucleotide primer pair; and (b) determining the amount amplified versus that for a normal CFTR gene promoter, wherein a substantial decrease or increase in the amount of detectable promoter segment observed over that for a normal CFTR gene promoter indicates a deletion or duplication of the CFTR promoter in the sample, wherein deletions or duplications, respectively, in the promoter region of the CFTR gene comprise at least four nucleotides.

Amplified target segments can be efficiently evaluated by size and/or detectable moiety using commercially available automated systems. For example, ABI PRISM® 3100 Genetic Analyzer can be used with an ABI PRISM 3100 capillary array, 36-cm (P/N#4315931). This provides a multi-color fluorescence-based DNA analysis system that uses capillary electrophoresis (CE) with 16 capillaries operating in parallel to separate labeled PCR products. A CE DNA sequencer/analyzer that operates 96 capillaries may be preferable in assays wherein 96-well plates are used. Analyzers with the capacity to process 96 wells include the MegaBACE™ 1000 DNA Analysis System (Molecular Dynamics, Inc and Amersham Pharmacia Biotech) and the 3700 DNA Analyzer from (Perkin-Elmer Biosystems).

The methods of detecting deletions or duplications of various exons of the CFTR gene may used for diagnosing a genetic basis for cystic fibrosis. Accordingly, there is provided a method for diagnosing a genetic basis for cystic fibrosis by analyzing a sample comprising nucleic acids; the method comprising: (a) amplifying target segments of the CFTR gene in a single tube using an oligonucleotide primer pair specific to each of the target segments; and (b) identifying the amplified target segments and determining the amount of each target segment amplified versus that for a normal CFTR gene, wherein a substantial decrease or increase in the amount of detectable target segment observed over that for a normal CFTR gene indicates a deletion or duplication, respectively, of the CFTR segment in the sample.

Disclosed are novel deletions involving the CFTR promoter region and associated upstream exon(s) that can be used in diagnosing a genetic basis for CF. Accordingly, a method is provided for diagnosing a genetic basis for cystic fibrosis (CF) by analyzing a sample comprising nucleic acids from an individual, the method comprising determining if the promoter region of the CFTR gene contains deleted or duplicated sequence involving four or more nucleotides, wherein the promoter region represents 250 nucleotides or more directly upstream of the CFTR start codon. These promoter/exon mutations include a deletion in a segment of the CFTR promoter region including the adjoining CFTR exon 1 or a deletion in a segment of the CFTR promoter region including the adjoining CFTR exons 1 and 2. The deletion involving the promoter region and exon 1 comprises at least 1,800 nucleotides in length of which at least 1,630 nucleotides represents sequence from the CFTR promoter region. The deletion involving the promoter and exons 1 and 2 comprises at least 28,000 nucleotides in length of which at least 3,570 nucleotides represents sequence from the CFTR promoter region. These deletions may be detected using the methods disclosed herein or other methods of deletion detection well known in the art.

Novel deletions involving CFTR exons 22, 23, and 24 but no other CFTR exons are disclosed herein for use in CF genetic testing. Sequence 3' to exon 24 also may be deleted with exons 22, 23 and 24. Accordingly, a method is provided for diagnosing a genetic basis for cystic fibrosis (CF) by analyzing a sample comprising nucleic acids from an individual, the method comprising determining if sample contains a CFTR gene in which CFTR exons 22, 23, and 24 are the only exons deleted. These deletions may be detected using the methods disclosed herein or other methods of deletion detection well known in the art.

The following examples serve to illustrate the present invention. These examples are in no way intended to limit the scope of the invention.

EXAMPLES

Example 1: Multiplex PCR Assay for CFTR Gene Segments

A. Extraction of DNA

Whole blood, amniotic fluid, cultured cells, and chorionic villi, are maintained preferably under ambient temperature (18-26° C.). Whole blood should be stable for 8 days at ambient temperature (18-26° C.) or 8 days refrigerated (2-8° C.). Optimally, DNA should be extracted amniotic fluid, cultured cells, or chorionic villi within 24 hours of receipt. Samples are preferably analyzed without freezing. Once extracted, DNA should be stable for 24-48 hours at 2-8° C. DNA should be frozen if longer storage is anticipated.

The following example describes a suitable procedure to prepare nucleic acids from blood. 50 µL of whole blood is mixed with 0.5 ml of TE (10 mM Tris HCl, 1 mM EDTA, pH 7.5) in a 1.5 mL microfuge tube. The sample is spun for 10 seconds at 13,000×g. The pellet is resuspended in 0.1 mL of TE buffer with vortexing, and pelleted again. This procedure is repeated twice more, and then the final cell pellet is resuspended in 100 µl of K buffer 50 mM KCl, 10 mM Tris HCl, 2.5 mM MgCl$_2$, 0.5% Tween 20, 100 µg/mL proteinase K, pH 8.3) and incubated 45 minutes at 56° C., then 10 minutes at 95° C. to inactivate the protease.

Alternative nucleic acid extraction methods can be used such as the Qiagen extraction method (Qiagen BioRobot 9604).

B. Preparation of CFTR-Multiplex PCR Primer Mix

A CFTR-multiplex PCR primer mix (4,550 µL) containing each of the primers for the CFTR multiplex PCR reaction was made by mixing stock solutions (100 µM) of each of the primers shown in Table 2. The table includes the volume of each primer and its final concentration in the PCR.

TABLE 2

CFTR and internal control primer concentrations in Master Mix

| Primer Name | x 1 rxn (ul) | 1000 | Final Conc in PCR Reaction uM | Size | Observed |
|---|---|---|---|---|---|
| TSF | 0.05 | Master | 0.2 | 140 | 137.6 |
| TSR | 0.05 | 50 | 0.2 | | |
| F2F | 0.05 | 50 | 0.2 | 332 | 331.9 |
| F2R | 0.05 | 50 | 0.2 | | |
| F5F | 0.05 | 50 | 0.2 | 212 | 210.4 |
| F5R | 0.05 | 50 | 0.2 | | |
| 18F | 0.1 | 100 | 0.4 | 297 | 296.1 |
| 18R2 | 0.1 | 100 | 0.4 | | |
| 3F2 | 0.05 | 50 | 0.2 | 128 | 124.2 |
| 3R | 0.05 | 50 | 0.2 | | |
| 11F | 0.025 | 25 | 0.1 | 132 | 127.2 |
| 11R | 0.025 | 25 | 0.1 | | |
| 21F | 0.05 | 50 | 0.2 | 136 | 132.7 |
| 21R | 0.05 | 50 | 0.2 | | |
| 14AF | 0.025 | 25 | 0.1 | 144 | 142.1 |
| 14AR | 0.025 | 25 | 0.1 | | |
| 2F | 0.05 | 50 | 0.2 | 154 | 153 |
| 2R | 0.05 | 50 | 0.2 | | |
| 5F | 0.05 | 50 | 0.2 | 159 | 157.4 |
| 5R | 0.05 | 50 | 0.2 | | |
| 20F | 0.05 | 50 | 0.2 | 162 | 161.8 |
| 20R | 0.05 | 50 | 0.2 | | |
| 6AF | 0.05 | 50 | 0.2 | 170 | 170.4 |
| 6AR | 0.05 | 50 | 0.2 | | |
| 22F | 0.05 | 50 | 0.2 | 176 | 176.6 |
| 22R | 0.05 | 50 | 0.2 | | |
| 24F | 0.05 | 50 | 0.2 | 187 | 183.6 |
| 24R | 0.05 | 50 | 0.2 | | |
| 17AF | 0.05 | 50 | 0.2 | 190 | 188.4 |
| 17AR | 0.05 | 50 | 0.2 | | |
| 23F | 0.05 | 50 | 0.2 | 193 | 191.6 |
| 23R | 0.05 | 50 | 0.2 | | |
| 9F | 0.1 | 100 | 0.4 | 318 | 317.4 |
| 9R | 0.1 | 100 | 0.4 | | |
| 14BF | 0.075 | 75 | 0.3 | 201 | 200.3 |
| 14BR | 0.075 | 75 | 0.3 | | |
| 8F2 | 0.075 | 75 | 0.3 | 216 | 215 |
| 8R | 0.075 | 75 | 0.3 | | |
| 12F | 0.075 | 75 | 0.3 | 208 | 205.9 |
| 12R | 0.075 | 75 | 0.3 | | |
| 6BF | 0.075 | 75 | 0.3 | 228 | 226.8 |
| 6BR | 0.075 | 75 | 0.3 | | |
| 4F | 0.075 | 75 | 0.3 | 237 | 236.9 |
| 4R | 0.075 | 75 | 0.3 | | |
| 10F | 0.075 | 75 | 0.3 | 745 | 245.5 |
| 10R | 0.075 | 75 | 0.3 | | |
| 19F | 0.075 | 75 | 0.3 | 250 | 248.7 |
| 19R | 0.075 | 75 | 0.3 | | |
| 13F | 0.1 | 100 | 0.4 | 253 | 253.3 |
| 13R | 0.1 | 100 | 0.4 | | |
| 17bF2 | 0.1 | 100 | 0.4 | 306 | 303.9 |
| 17bR2 | 0.1 | 100 | 0.4 | | |
| 15F | 0.1 | 100 | 0.4 | 262 | 261.6 |
| 15R | 0.1 | 100 | 0.4 | | |
| 7F | 0.1 | 100 | 0.4 | 267 | 267.1 |

TABLE 2-continued

CFTR and internal control primer concentrations in Master Mix

| Primer Name | x 1 rxn (ul) | 1000 | Final Conc in PCR Reaction uM | Size | Observed |
|---|---|---|---|---|---|
| 7R | 0.1 | 100 | 0.4 | | |
| 1F | 0.1 | 100 | 0.4 | 272 | 272 |
| 1R | 0.1 | 100 | 0.4 | | |
| P1F | 0.1 | 100 | 0.4 | 287 | 288.2 |
| P1R | 0.1 | 100 | 0.4 | | |
| UpEx9F | 0.1 | 100 | 0.4 | 118 | 113.6 |
| UpEx9R | 0.1 | 100 | 0.4 | | |
| 16F | 0.15 | 150 | 0.6 | 281 | 280.9 |
| 16R | 0.15 | 150 | 0.6 | | |
| Total | 4.55 | 4550 | | | |

A multiplex PCR that can verify a suspected CFTR promoter deletion or duplication and asses the extent of such deletion or duplication may be performed using the mixture of primers shown in Table 3. The amount of each primer in the amplification is listed in Table 3 along with the expected size of the fragment. The promoter deletion/duplication verification PCR primer mix (1,025 µL) was made by mixing stock solutions (100 µM) of each of the primers shown in Table 3. The sequences of these primers can be found in Tables 1 and 2. In addition to the three promoter primers upstream of the first promoter primer set, the master mix includes primers for the three internal controls and primer pairs for CFTR exons 1-4.

TABLE 3

CFTR promoter deletion/duplication verification primer master mix

| Primer Name | x 1 rxn (ul) | 200 | Final Conc in PCR Reaction uM | Size Expected |
|---|---|---|---|---|
| TSF | 0.05 | 10 | 0.2 | 140 |
| TSR | 0.05 | 10 | 0.2 | |
| F2F | 0.05 | 10 | 0.2 | 332 |
| F2R | 0.05 | 10 | 0.2 | |
| F5F | 0.05 | 10 | 0.2 | 212 |
| F5R | 0.05 | 10 | 0.2 | |
| UpPr1F | 0.05 | 10 | 0.2 | 230 |
| UpPr1R | 0.05 | 10 | 0.2 | |
| 3F2 | 0.025 | 5 | 0.1 | 132 |
| 3R | 0.025 | 5 | 0.1 | |
| UpPr2F1 | 0.025 | 5 | 0.1 | 202 |
| UpPr2R | 0.025 | 5 | 0.1 | |
| 21F | 0.025 | 5 | 0.1 | 136 |
| 21R | 0.025 | 5 | 0.1 | |
| 2F | 0.025 | 5 | 0.1 | 154 |
| 2R | 0.025 | 5 | 0.1 | |
| UpPr3F | 0.025 | 5 | 0.1 | 188 |
| UpPr3R | 0.025 | 5 | 0.1 | |
| 4F | 0.0375 | 7.5 | 0.15 | 237 |
| 4R | 0.0375 | 7.5 | 0.15 | |
| 1F | 0.075 | 15 | 0.3 | 272 |
| 1R | 0.075 | 15 | 0.3 | |
| P1F | 0.075 | 15 | 0.3 | 287 |
| P1R | 0.075 | 15 | 0.3 | |
| Total | 1.025 | 205 | | |

C. Amplification from DNA

Individual amplifications were prepared in a volume of 25 µl. Each amplification volume contained 4 µl of the DNA sample (generally 10-100 ng of DNA), 20.6 µl of CFTR Master Mix, and 0.4 µl of FasStar Taq (Roche Applied science, Cat. No. 2 032 937). In another approach, individual amplifications were prepared in a volume of 12.5 µl. Each amplification volume contained 2 µl of the DNA sample (generally 10-100 ng/µl of DNA), 10.3 µl of CFTR master mix and 0.2 µl of FasStar Taq (Roche Applied Science, Cat no. 2032937).

Master mix contained the CFTR-multiplex PCR primer mix, Roche PCR buffer with $MgCl_2$, Roche GC rich solution (cat. No. 2 032 937), bovine serum albumin (BSA) (New England BioLabs, Cat no. B9001B), and NTPs (Amersham Biosciences, Cat no. 27-2032-01). The final concentration in the PCR for $MgCl_2$ was 2.859 mM, for BSA was 0.725 µg/µl, and for each dNTP was 0.362 mM. The PCR master mix for the full multiplex of primers in Table 1 is shown in Table 4. The PCR master mix for the full multiplex of promoter region primers and controls in Table 3 is shown in Table 5

TABLE 4

CFTR PCR master mix

| Reagent | X 1 rxn (ul) | 1000 | Final Conc in PCR Reaction mM |
|---|---|---|---|
| FS 10X w/o $MgCl_2$ | 5 | 5000 | 2X |
| $MgCl_2$ | 4 | 4000 | 4 |
| 25 mM dNTP | 0.4 | 400 | 0.4 |
| Primer MIX | 4.55 | 4550 | |
| GC rich | 2.5 | 2500 | 1X |
| BSA (10 mg/ml) | 1 | 1000 | 0.4 ug/ul |
| Water | 3.15 | 3150 | |
| Total | 20.6 | 20600 | |

TABLE 5

CFTR Promoter region Master mix

| Reagent | x 1 rxn (ul) | 200 | Final Conc in PCR Reaction mM |
|---|---|---|---|
| FS 10X w/o MgCl2 | 2.5 | 500 | 2X |
| MgCl2 | 2 | 400 | 2 |
| 25 mM dNTP | 0.2 | 40 | 0.2 |
| Primer MIX | 1.025 | 205 | |
| GC rich | 1.25 | 250 | 1X |
| BSA (10 mg/ml) | 0.5 | 100 | 0.4 ug/ul |
| Water | 2.825 | 565 | |
| Total | 10.3 | 2060 | |

PCR was conducted using the following temperature profile: step 1: 95° C. for 5 minutes; step 2: 94° C. for 15 seconds; step 3: decrease at 0.5° C./second to 56° C.; step 4: 56° C. for 1 minute and 10 seconds; step 5: increase at 0.5° C./second to 72° C., step 6: 72° C. for 45 seconds +5 seconds additional per additional cycle; step 7: increase 0.5° C. up to 94° C.; step 8: repeat steps 2 to 7 twenty one times; step 9: 72° C. for 5 minutes; step 10: 60° C. for 75 min, step 11: 4° C. hold (to stop the reaction).

D. Detection and Analysis of Amplified Product

2 µL of each PCR product was added to 10.5 µL Hi-Di-Rox 350 mix and loaded onto a ABI 3100 Genetic Analyzer for separation. Alternatively, electrophoresis can be performed by subjecting the amplified product to gel electrophoresis such as an agarose gel electrophoresis. The primers may need to be labeled with a detectable label to enhance the sensitivity of detection in some gel systems.

The data corresponding to the amplified nucleotide segments from the ABI3100 were analyzed using GeneMapper software. The observed size and color of each target segment amplified from normal DNA using the primer set shown in Table 1 is shown in Table 6. FAM is blue and HEX is green.

TABLE 6

Analysis of amplified CFTR exons and internal controls

| CFTR exon/intron or internal control | Size | Observed size | DYE |
|---|---|---|---|
| UpEx 9 | 118 | 113.6 | Green |
| Ex 3 | 128 | 124.2 | Blue |
| Ex 11 | 132 | 127.2 | Blue |
| Ex 21 | 136 | 132.7 | Blue |
| Tay-Sachs | 140 | 137.6 | Green |
| Ex 14a | 144 | 142.1 | Blue |
| Ex 2 | 154 | 153 | Blue |
| Ex 5 | 159 | 157.4 | Blue |
| Ex 20 | 162 | 161.8 | Blue |
| Ex 6a | 170 | 170.4 | Blue |
| Ex 22 | 176 | 176.6 | Blue |
| Ex 24 | 187 | 183.6 | Blue |
| Ex 17a | 190 | 188.4 | Blue |
| Ex 23 | 193 | 191.6 | Blue |
| Ex 14b | 201 | 200.3 | Blue |
| Ex 12 | 208 | 205.9 | Blue |
| Factor 5 | 212 | 210.4 | Green |
| Ex 8 | 216 | 215 | Blue |
| Ex 6b | 228 | 226.8 | Blue |
| Ex 4 | 237 | 236.9 | Blue |
| Ex 10 | 245 | 245.5 | Blue |
| Ex 19 | 250 | 248.7 | Blue |
| Ex 13 | 253 | 253.3 | Blue |
| Ex 15 | 262 | 261.6 | Blue |
| Ex 7 | 267 | 267.1 | Blue |
| Ex 1 | 272 | 272 | Blue |
| Ex 16 | 281 | 280.9 | Blue |
| Promoter | 287 | 288.2 | Blue |
| Ex 18 | 297 | 296.1 | Blue |
| Ex 17b | 306 | 303.9 | Blue |
| Ex 9 | 318 | 317.4 | Blue |
| Factor 2 | 332 | 331.9 | Blue |

The signal for each of the above amplicons observed for DNA from a sample with an unknown CFTR genotype is compared with the amount of the corresponding amplified segment observed for DNA from an individual with a wildtype CFTR gene. The GeneMapper software is used to analyze data generated from the ABI 3100. An Excel report is uploaded into a database that will score the results and generate automated allele calls.

A deletion of one or more exons will be shown by a drop in the intensity of the fragment(s) by at least 30-50%, of the normal (wildtype CFTR exon) signal while a duplication will show an increase to at least 130-150% of the normal (wildtype CFTR exon) signal.

For best results, sample DNA for unknown CFTR genotype should be amplified in parallel with positive control sample containing wt/wt CFTR genotype and/or wt/mut genotype for CF carriers.

Negative Controls Included;
  a) NS Control: a reagent blank (NS control) comprises all reagents and processing used to prepare sample DNA but without any starting DNA; and
  b) ND Control: A minus DNA control (ND control) is used which consists of a PCR kit and polymerase mix used for the assay run.

Positional Control: a QC blank is placed randomly within each plate to ensure results reflect the correct positioning of the Extraction/PCR plate for detection.

Negative controls should display no significant amplification and/or fluorescent signal. If the reagent blank (NS control) shows evidence of significant amplification, all the patient samples associated with that NS control are potentially contaminated. If the minus DNA control (ND control) yields significant amplification, the PCR amplification reagents are potentially contaminated. Note that the existing PCR master reaction mix may be the source of the contamination. Specimens my need to be re-extracted and re-assayed (NS) and the entire assay repeated (ND).

Negative control DNAs should display no significant fluorescent signal upon electrophoresis on an ABI3100 genetic analyzer. If the NS control shows evidence of significant fluorescence, all the patient samples associated with that NS control are potentially contaminated.

The QC Blank control should display no significant signal.

Example 2: Evaluating Samples from Individuals to Determine a Genetic Basis for CF Samples from patients with a mutant CF gene were evaluated for CF deletion or duplication analysis in accordance with the methods herein. Several samples with rearrangements were identified. A deletion encompassing the CFTR promoter, and exons 1 and 2 was detected in one sample, with the same mutation detected in the maternal DNA. In another family, a deletion of the promoter and exon 1 was detected in three siblings. In both of these cases, the families were African-American, and a 3120+1G>A splice site mutation was identified. These deletions have not been previously described. In a third case involving a Caucasian patient, a deletion of exons 17a, 17b and 18 was identified and the same mutation was detected in the paternal DNA. In four other cases, deletions in exons 2 and 3; exons 4, 5 and 6a; exons 17a and 17b; and a deletion of exons 22, 23 and 24 were identified. These mutations would remove parts of transmembrane domain 1, transmembrane domain 2, or the second Nucleotide Binding Domain. In patients diagnosed with "classic CF" submitted for sequencing analysis, 20% harbored rearrangements, accounting for 10% of CF chromosomes. Classic CF is characterized by elevated sweat chloride, lung and pancreatic insufficiency, failure to thrive, and in most male cases, and congenital bilateral absence of the vas deferens (CBAVD). The frequency of occurrence of rearrangements in CF patients when only one mutation is identified by DNA sequencing is 50%. It is possible that complex abnormalities may account for a significant proportion of CF chromosomes in the general population. The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

That which is claimed is:

1. A method of detecting a deletion of exon 22, exon 23 and exon 24 in a human cystic fibrosis transmembrane regulatory (CFTR) gene comprising:
   (a) contacting a nucleic acid sample comprising a human CFTR nucleic acid with oligonucleotide primer pairs to amplify at least one target segment from each of exons 22, 23 and 24 of a human CFTR gene, wherein at least one primer of each oligonucleotide primer pair is detectably labeled;
   (b) detecting labeled amplicons for each target segment produced in (a);
   (c) quantitating an amount of labeled amplicons detected for each target segment;
   (d) comparing the amount of labeled amplicons for each target segment with a corresponding control amount for each target segment, wherein the corresponding control amount is obtained by amplifying the target segments of step (a) in a nucleic acid sample comprising a wildtype human CFTR gene using the same oligonucleotide primer pairs;
   (e) identifying the deletion of exon 22, exon 23 and exon 24 in one or both alleles of the CFTR gene when the amount of labeled amplicons for each target segment quantified in step (c) is at least 30% less than the control amount, wherein detection of a deletion of a target segment in each of exons 22, 23, and 24 indicates that exons 22, 23, and 24 are deleted,
   wherein the oligonucleotide primer pair for amplification of
     (i) a target segment of exon 22 of the CFTR gene consists of a forward primer comprising the sequence of SEQ ID NO: 51 and a reverse primer comprising the sequence of SEQ ID NO: 52;

(ii) a target segment of exon 23 of the CFTR gene consists of a forward primer comprising the sequence of SEQ ID NO: 53 and a reverse primer comprising the sequence of SEQ ID NO: 54; or (iii) a target segment of exon 24 of the CFTR gene consists of a forward primer comprising the sequence of SEQ ID NO: 55 and a reverse primer comprising the sequence of SEQ ID NO: 56.

2. The method of claim 1 wherein the human CFTR nucleic acid is genomic DNA.

3. The method of claim 1 wherein the human CFTR nucleic acid is mRNA.

4. The method of claim 1 wherein amplifying involves a multiplex polymerase chain reaction.

5. The method of claim 1, wherein the amplifying employs the oligonucleotide primers of SEQ ID NOs: 51, 52, 53, 54, 55 and 56.

6. The method of claim 1, wherein the oligonucleotide primer pair for amplification of a target segment of exon 22 of the CFTR gene consists of a forward primer comprising the sequence of SEQ ID NO: 51 and a reverse primer comprising the sequence of SEQ ID NO: 52.

7. The method of claim 1, wherein the oligonucleotide primer pair for amplification a target segment of exon 23 of the CFTR gene consists of a forward primer comprising the sequence of SEQ ID NO: 53 and a reverse primer comprising the sequence of SEQ ID NO: 54.

8. The method of claim 1, wherein the oligonucleotide primer pair for amplification a target segment of exon 24 of the CFTR gene consists of a forward primer comprising the sequence of SEQ ID NO: 55 and a reverse primer comprising the sequence of SEQ ID NO: 56.

9. The method of claim 1, wherein detection of the labeled amplicons involves separating the labeled amplicons by size.

10. The method of claim 1, wherein size separation is performed by gel electrophoresis.

11. The method of claim 1, wherein at least one primer of each said primer pair is labeled with a fluorescent dye.

* * * * *

SEQUENCE LISTING

```
<160> NUMBER OF SEQ ID NOS: 70

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
actgtcgccc acctgcgg                                                        18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccgcacacca ccccttcc                                                        18

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aattggaagc aaatgacatc acag                                                 24

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttcctttacc ccaaacccaa                                                      20

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
```
cctctcttta ttttagctgg accagac                    27

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcaactaaac aatgtacatg aacatacct                    29

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaatgggata gagagctggc t                    21

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgtacaaatg agatccttac ccta                    25

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gaagtcacca agcagtaca gcc                    23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcctgtgcaa ggaagtatta cct                    23

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tttagacttt aaagctgtca agccg                    25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
ccgcctttcc agttgtataa tttat    25

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
ggacttgcat tggcacattt    20

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
tgctacctgt acttcatcat cattc    25

<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
tgtaaaacga cggccagtag atcagagagc tgggaagatc a    41

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
ggtggaagtc taccatgata aacat    25

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
aacagaactg aaactgactc gga    23

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcagcattat ggtacattac ctgta                                         25

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tttttttttt tttttataag atgtagcaca atgagagtat aaagt                   45

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
taaaaattct gacctcctcc ca                                            22

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tggatcatgg gccatgtgc                                                19

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
caaaagaact accttgcctg ct                                            22

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tccagacttc acttctaatg gtga                                          24

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
gtgaagggtt catatgcata atcaa                                         25

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
aggacatctc caagtttgca ga                                            22

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
gcaaatgctt gctagaccaa taatt                                         25

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
tgaccaggaa atagagagga aatg                                          24

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
ctatgatggg acagtctgtc tttct                                         25

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
gtgatcagca ctggccccac                                               20

<210> SEQ ID NO 30

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cccccaagcg atgtatacct                                              20

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ttttgagtgc tttttttgatg atatggaga                                   29

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aacattctta cctctgccag aaaa                                         24

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggaggaatag gtgaagatgt tagaa                                        25

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ggagaaatga aacaaagtgg attac                                        25

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35 tttttttca ctcctcttca agacaaaggg                                    30

<210> SEQ ID NO 36
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tacctgcttt caacgtgttg ag                                              22

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gcgtctactg tgatccaaac ttagt                                           25

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ggacttcaac cctcaatcaa ataaa                                           25

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ttctcaccaa catgttttct ttgatc                                          26

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gtcatacctt cagattccag ttgtt                                           25

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tggaaatatt tcacaggcag gagtc                                           25

<210> SEQ ID NO 42
<211> LENGTH: 33
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 42
cattttattc attgaaaatt ttttacttaa atg                          33

<210> SEQ ID NO 43
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tacttactat atgcagagca ttattctatt agtag                        35

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cttaccaagc tatccacatc tatgc                                   25

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
atgcgatctg tgagccgagt                                         20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ccctctggcc aggacttatt                                         20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gtgggcctct tgggaagaac                                         20

<210> SEQ ID NO 48
<211> LENGTH: 23
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 48
gctcacctgt ggtatcactc caa                                          23

<210> SEQ ID NO 49
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tgtaaaacga cggccagtct tttctttttt gctatagaaa gtatttattt t           51

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cagccttacc tcatctgcaa ctt                                          23

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gttgggctca gatctgtgat aga                                          23

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cacactggat ccaaatgagc ac                                           22

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
cattactgtt ctgtgatatt atgtgtggta                                   30

<210> SEQ ID NO 54
<211> LENGTH: 24
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 54
caagggcaat gagatcttaa gtaa                                          24

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
agaagagaac aaagtgcggc a                                             21

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tgtatcttgc acctcttctt ctgtc                                         25

<210> SEQ ID NO 57
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
tttttttttt tgtaaaacga cggccagttt cagtctttac tgaaattaaa aaatctt      57

<210> SEQ ID NO 58
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
atagcatacg gtttctagag gacatg                                        26

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ttgaaggaaa tgccccatta tttagccagg                                    30

<210> SEQ ID NO 60
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
tgcttaacaa gaccatacta cagtgacgt                               29

<210> SEQ ID NO 61
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
aggaggacct gtcctcccag atggt                                   25

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ctgtccagcc aggagacccc a                                       21

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
cattcttacc tggtccccag gacaaag                                 27

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gtcctacaac cctgtcaccc acatc                                   25

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gaattcaaag gaaaacataa gatgcaattc                              30

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 66
aacacacatt acagtcttac aaagatgttt                                          30

<210> SEQ ID NO 67
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ccacactaac agttataaac caaacaaca                                           29

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
caccaggaaa gaatttcagc attt                                                24

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ctaaaacact ccaaagcctt cctt                                                24

<210> SEQ ID NO 70
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ttcaggttta ggtgagtgaa ctccaa                                              26
```